United States Patent
Zygmunt et al.

(10) Patent No.: US 6,452,025 B1
(45) Date of Patent: Sep. 17, 2002

(54) THREE-STEP CONVERSION OF PROTECTED TAXANE ESTER TO PACLITAXEL

(75) Inventors: Jan Zygmunt, Longmont; James D. McChesney, Boulder, both of CO (US)

(73) Assignee: NaPro BioTherapeutics, Inc., Boulder, CO (US)

( * ) Notice: Subject to any disclaimer, the term of this patent is extended or adjusted under 35 U.S.C. 154(b) by 0 days.

(21) Appl. No.: 09/843,235

(22) Filed: Apr. 25, 2001

(51) Int. Cl.$^7$ ............................................. C07D 305/14
(52) U.S. Cl. ....................................... 549/510; 549/511
(58) Field of Search .................................. 549/510, 511

(56) References Cited

U.S. PATENT DOCUMENTS

| | | | |
|---|---|---|---|
| 4,814,470 A | 3/1989 | Colin et al. | |
| 4,857,653 A | 8/1989 | Colin et al. | |
| 4,924,011 A | 5/1990 | Denis et al. | |
| 4,924,012 A | 5/1990 | Colin et al. | |
| 4,960,790 A | 10/1990 | Stella et al. | |
| 5,015,744 A | 5/1991 | Holton | |
| 5,136,060 A | 8/1992 | Holton | |
| RE34,277 E | 6/1993 | Denis et al. | |
| 5,319,112 A | * 6/1994 | Kingston et al. | 549/510 |
| 5,684,175 A | 11/1997 | Sisti et al. | |
| 5,750,737 A | 5/1998 | Sisti et al. | |
| 5,770,745 A | 6/1998 | Swindell et al. | |
| 5,939,566 A | * 8/1999 | Swindell et al. | 549/510 |
| 5,973,170 A | 10/1999 | Sisti et al. | |

FOREIGN PATENT DOCUMENTS

| | | |
|---|---|---|
| EP | 0 400 971 | 12/1990 |
| EP | 0 528 729 A1 | 2/1993 |
| FR | 2 687 150 | 8/1993 |
| WO | WO 91/13066 | 9/1991 |
| WO | WO 94/18186 | 8/1994 |

OTHER PUBLICATIONS

"Biologically Active Taxol Analogues with Deleted A–Ring Side Chain Substituents and Variable C–2' Configurations", Swindell et al, *Journal of Medicinal Chemistry*, 1991, vol. 34, No. 3, pp. 1176–1184.

"New and Efficient Approaches to the Semisynthesis of Taxol and Its C–13 Side Chain Analogs by Means of B–Lactam Synthon Method", Ojima et al, *Tetraheron*, vol. 48, No. 34, pp. 6985–7012, 1992.

"Improved Protection and Esterification of a Precursor of the Taxotere and Taxol Side Chains", Commercon et al, *Tetrahedron Letters*, vol. 33, No. 36, pp. 5185–5188, 1992.

"Highly Stereocontrolled and Efficient Preparation of the Protected, Esterification–Ready Docetaxel (Taxotere) Side Chain", Kanazawa et al, *J. Org. Chem*, vol. 59, No. 6, pp. 1238–1240, 1994.

"Novel Biologically Active Taxol Analogues: Baccatin III 13–(N–(p–Chlorobenzoyl)–(2'R,3'S)–3'–phenylisoserinate) and Baccatin III 13–N–Benzoyl–(2'R, 3'S)–3'–(p–chlorophenyl) isoserinate)", Georg et al., *Bioorganic & Medicinal Chemistry Letters*, vol. 2, No. 4, pp. 295–298, 1992.

"Application of the Vicinal Oxyamination Reaction with Asymmetric Induction to the Hemisynthesis of Taxol and Analogues", L. Mangatal et al., *Tetrahedron*, vol. 45, No. 13, pp. 4177 to 4190, 1990.

"Synthesis of Biologically Active Taxol Analogues with Modified Phenylisoserine Side Chains", Georg et al., *J. Med. Chem.*, 1992, 35, 4230–4237.

"Selectively Reductive Cleavage of the Protected Taxol Side Chain with Sodium Borohydride", *Chemical Abstracts*, vol. 125, No. 21, 1996, C.Z., Yu et al, Abstract No. 276128j, p. 1302.

"Selectively Reductive Cleavage of the Protected Taxol Side Chain with Sodium Borohydride", *Chinese Journal of Chemistry*, vol. 14, No. 4, 1996, pp. 381–384.

"Taxol Chemistry. 7–O–Triflates as precursors to Olefins and Cyclopropanes," Johnson et al., *Tetrahedron Letters*, vol. 35, No. 43, pp. 7893–7896, 1994.

"Alkyl Benzyl Carbonate: ROCO$_2$Bn (Chart 2)," *Protective Groups in Organic Synthesis*, Greene et al., 2d ed., p. 109, 1991.

* cited by examiner

Primary Examiner—Ba K. Trinh
(74) *Attorney, Agent, or Firm*—Timothy J. Martin; Michael R. Henson; Mark H. Weygandt

(57) ABSTRACT

The present invention relates to a method of producing paclitaxel from a protected coupled ester compound having a formula:

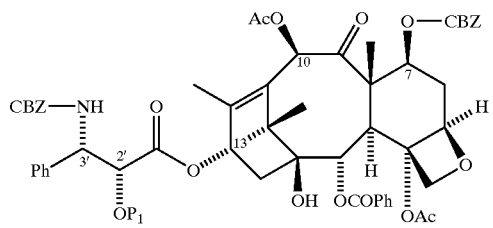

wherein $P_1$ is a hydrogenatable protecting group, comprising deprotecting the 7-O-position and 3'-N-position of the protected coupled ester compound to form a first intermediate compound, benzoylating the first intermediate compound at the 3'-N-position thereby to form a second intermediate compound, and deprotecting the second intermediate compound by replacing $P_1$ with hydrogen in the presence of an acid. The present invention also provides chemical compounds useful in the production of paclitaxel.

34 Claims, 3 Drawing Sheets

THREE-STEP CONVERSION OF PROTECTED TAXANE ESTER TO PACLITAXEL

FIELD OF THE INVENTION

The present invention is directed to the production of the anti-neoplastic compound paclitaxel. More particularly, the present invention is directed to the production of paclitaxel from a protected coupled ester intermediate, which may be formed by esterifying a protected baccatin III backbone with a suitably protected side chain acid. In particular, the present invention relates to the production of paclitaxel by esterifying 7-CBZ baccatin III with a 3-N-CBZ-2-O-protected-(2R,3S)-3-phenylisoserine to produce a protected coupled ester intermediate that may thereafter be deprotected and N-benzoylated to produce paclitaxel.

BACKGROUND OF THE INVENTION

Various taxane compounds are known to exhibit anti-tumor activity. As a result of this activity, taxanes have received increasing attention in the scientific and medical community. Primary among these is a compound known as "paclitaxel" which is also referred to in the literature as "taxol". Paclitaxel has been approved for the chemotherapeutic treatment of several different varieties of tumors, and the clinical trials indicate that paclitaxel promises a broad range of potent anti-leukemic and tumor-inhibiting activity. Paclitaxel has the formula:

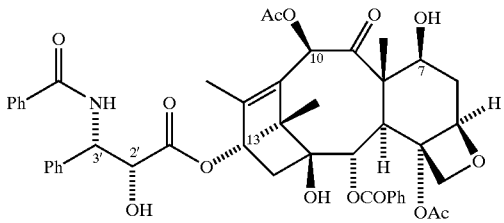

Paclitaxel is a naturally occurring taxane diterpenoid which is found in several species of the yew (genus Taxus, family Taxaceae). Unfortunately, the concentration of this compound in the yew is very low, and the species of evergreen are also slow growing. Even though the bark of the yew trees typically exhibit the highest concentration of paclitaxel, the production of one kilogram of paclitaxel requires approximately 16,000 pounds of bark. Thus, the long-term prospects for the availability of paclitaxel through isolation are discouraging.

While the presence of paclitaxel in the yew tree is in extremely low concentrations, there are a variety of other taxane compounds, such as baccatin III, cephalomanine, 10-deacetylbaccatin III, etc., which are also able to be extracted from the yew bark and leaves. Some of these other taxane compounds are more readily extracted in higher yields. Indeed, a relatively high concentration of 10-deacetylbaccatin III can be extracted from the leaves of the yew as a renewable resource.

Accordingly, attention has turned to the semi-synthesis of paclitaxel from precursor compounds. In order to successfully synthesize paclitaxel, convenient access to a chiral, non-racemic side chain acid and an abundant natural source of a usable baccatin III backbone as well as an effective means of joining the two are necessary. However, the esterification of the side chain acid to the protected baccatin III backbone is difficult because of the steric hindrance of the 13-hydroxyl which is located in the baccatin III backbone within the concave region of the hemispherically shaped baccatin III skeleton.

Some early synthetic routes in the semi-synthesis of paclitaxel are described, for example, in U.S. Pat. No. 5,770,745 to Swindell et al. The use of protecting groups to protect various positions of the taxane backbone and the side chain acid was investigated as a means of improving the chemical process to form paclitaxel, and of improving the esterification step in particular.

One technique for the semi-synthesis of paclitaxel is found in U.S. Pat. No. 5,750,737 to Sisti et al. As discussed therein, paclitaxel can be synthesized by joining 7-CBZ baccatin III of the formula:

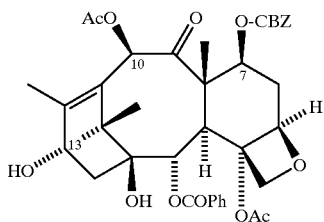

(where CBZ is the "benzyloxycarbonyl" group, $-CO_2CH_2Ph$), with 3-N-CBZ-2-O-protected (2R,3S)-3-phenylisoserine of the formula:

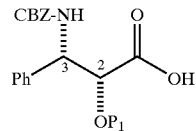

where the 2-hydroxyl is protected by a hydrogenatable benzyl-type group $P_1$ such as benzyloxymethyl (BOM) or benzyl. 7-CBZ baccatin III may be formed through the synthesis and use of 7-metal alkoxide intermediates and analogs of baccatin III, as described, for example, in U.S. Pat. Nos. 5,750,737 and 5,973,170 to Sisti et al. The production of the 3-N-CBZ-2-O-protected (2R,3S)-3-phenylisoserine is taught, for example, in U.S. Pat. No. 5,684,175 to Sisti et al.

Following the esterification of the protected baccatin III with the protected side chain to form a protected coupled ester of the formula:

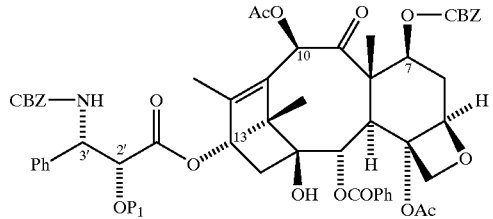

the compound may be suitably deprotected, acylated, and further deprotected to yield paclitaxel. Specifically, the CBZ protecting groups at the 7-O and 3'-N positions are removed, a benzoyl group is added at the 3'-N position and the 2'-O-protecting group is removed. U.S. Pat. No. 5,750,737 describes a deprotection and acylation sequence involving various steps to arrive at the final desired product. In particular, that patent teaches the use of work-ups involving recovery and purification steps (such as filtration, reduction to residue under vacuum, organic phase separation, and the like) in between the various steps. Furthermore, the hydrogenolysis of the coupled ester with Pearlman's catalyst as described therein could take about one day to proceed to completion of the deprotection at the 7-O and the 3'-N positions by removal of the two CBZ groups. Additionally, after benzoylation of the 3'-amino group, the hydrogenolysis of the 2'-O-BOM paclitaxel took several days to complete, and included catalyst replacement as well as isolation and purification of the 2'-O-BOM paclitaxel intermediate. Additionally, factors such as preliminary purification of the 2'-O-BOM-paclitaxel intermediate as well as change of the catalyst and reaction medium contribute to high cost of the hydrogenation process.

While the existing techniques for synthesizing paclitaxel certainly have merit, there is still a need for improved chemical processes that can produce this anti-cancer compound and intermediates useful in the synthesis and semi-synthesis thereof. In particular, it is desirable to provide efficient processes requiring shorter times and fewer steps while still providing acceptable yields in the semi-synthesis of paclitaxel. Accordingly, the present invention is directed to an improved synthesis of paclitaxel or other taxanes from a protected coupled ester intermediate. The present invention teaches a new, useful and more efficient method for the conversion of the protected coupled ester to paclitaxel that may be performed in a single reaction vessel.

SUMMARY OF THE INVENTION

It is an object of the present invention to provide a new and useful method for synthesizing paclitaxel.

It is another object of the present invention to provide new intermediate compounds useful in the production of paclitaxel.

It is a further object of the present invention to produce a protected coupled ester of the formula:

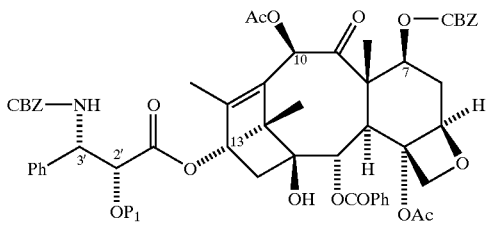

wherein $P_1$ is a hydrogenatable protecting group, such as a benzyl, substituted benzyl, benzyloxymethyl or benzoyl group, which may then be deprotected, and N-acylated and further deprotected to yield paclitaxel.

It is yet another object of the present invention to provide methods for producing paclitaxel which are simplified and which may be suitable for large scale production of paclitaxel for anti-neoplastic applications.

It is yet another object of the present invention to improve the efficiency of the hydrogenolytic conversion of a protected coupled ester to paclitaxel.

It is yet another object of the present invention to convert a protected coupled ester to paclitaxel in a single vessel without isolation or purification of a 2'-O-protected paclitaxel intermediate.

According to the present invention, then, a method is provided of producing paclitaxel from a protected coupled ester compound having a formula:

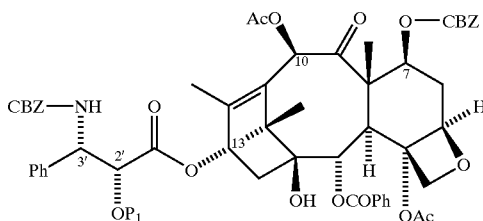

wherein $P_1$ is a hydrogenatable protecting group, such as a benzyl, substituted benzyl, benzyloxymethyl, or benzoyl group. The method comprises the steps of deprotecting 7-O-position and 3'-N-position of the protected coupled ester compound to form a first intermediate compound having a formula:

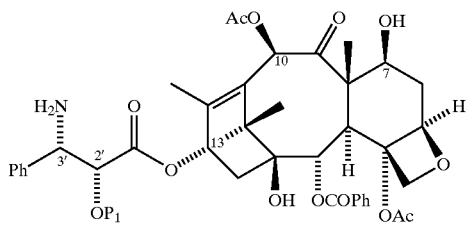

benzoylating said first intermediate compound at the 3'-nitrogen position thereby to form a second intermediate compound having the formula:

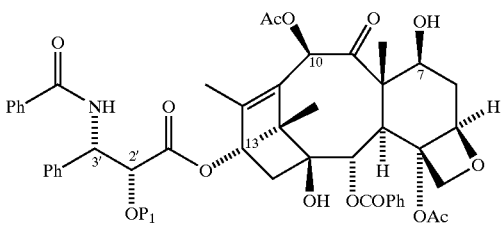

and deprotecting said second intermediate compound by replacing the $P_1$ protecting group with hydrogen in the presence of an acid, thereby to produce paclitaxel. $P_1$ may preferably be a benzyl, substituted benzyl, benzyloxymethyl, or benzoyl group. The protected coupled ester compound may be dissolved in a solvent, such as THF, to form a first solution, to which may be added water and a catalyst, such as a palladium on carbon catalyst, to form a first reaction mixture. The catalyst may be added in an amount of 30% to 80% mass equivalent of the protected coupled ester. The water may be added in an amount of 10 10% to 25% by volume of THF used. The step of deprotecting the 7-O-position and the 3'-N-position of the protected coupled ester compound may be accomplished by stirring the first reaction mixture under a hydrogen atmosphere for 30 to 60 minutes.

The step of N-benzoylating the first intermediate compound may be accomplished by mixing benzoic anhydride, preferably in 1.20 to 2.40 mol equivalents, with the first intermediate compound to form a second reaction mixture, and stirring the second reaction mixture for 30 to 60 minutes.

The step of deprotecting the second intermediate compound may be accomplished by mixing the second intermediate compound with a selected quantity, such as 5 to 20 mol equivalents, of the acid thereby to form a third reaction mixture, and thereafter stirring the third reaction mixture under a hydrogen atmosphere for one to five hours. The acid may be an inorganic or organic acid, and is preferably sulfuric acid or hydrochloric acid.

The present invention also relates to a method of producing paclitaxel which comprises the steps of stirring a first reaction mixture of a solvent, water, a catalyst and a protected coupled ester compound in a reaction vessel under a hydrogen atmosphere, adding a benzoylating agent to the reaction vessel to form a second reaction mixture, which may be stirred under an inert atmosphere, adding acid to the reaction vessel to form a third reaction mixture, and stirring the third reaction mixture in the reaction vessel under a hydrogen atmosphere thereby to produce paclitaxel.

The present invention is further directed to a process of producing paclitaxel from a protected coupled ester compound consisting of the steps of replacing the 7-O-CBZ and 3'-N-CBZ groups with hydrogen to form a first intermediate compound, benzoylating the first intermediate compound at the 3'-nitrogen position thereby to form a second intermediate compound, and replacing $P_1$ with hydrogen, thereby to produce paclitaxel.

Additionally, the present invention is directed to a chemical compound useful in the production of paclitaxel, having the formula:

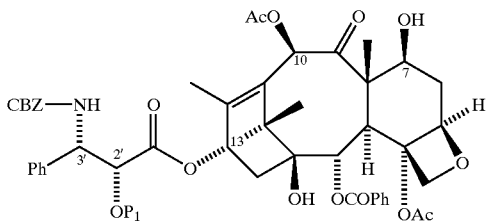

and to a chemical compound having the formula:

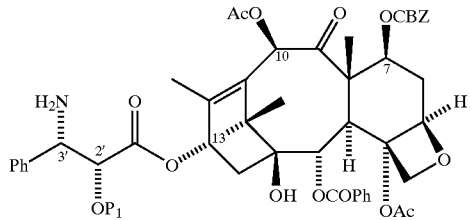

wherein $P_1$ is a hydrogenatable protecting group, such as a benzyl, substituted benzyl, benzyloxymethyl or benzoyl group.

These and other objects of the present invention will become more readily appreciated and understood from consideration of the following detailed description of the exemplary embodiments.

DETAILED DESCRIPTION OF THE INVENTION

The present invention is broadly directed to a new and useful chemical process for the production of paclitaxel and analogs thereof from a protected coupled ester intermediate. More specifically, the present invention provides an improvement to the chemical conversion of the protected coupled ester to paclitaxel, as described in U.S. Pat. No. 5,750,737 to Sisti et al.

In particular, Sisti et al. discusses the formation of a protected coupled ester intermediate, which can have a formula as follows:

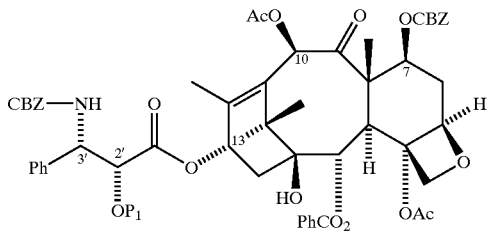

where $P_1$ is a hydrogenatable benzyl-type protecting group. The coupled ester intermediate is then converted into paclitaxel by removing the 7-O-CBZ and 3'-N-CBZ protecting groups, benzoylating the amino group at the 3' position, and removing the 2'-O-benzyl-type protecting group. As discussed in Sisti et al., this is accomplished by first dissolving the coupled ester in isopropanol, adding Pearlman's catalyst, and hydrogenating for twenty-four hours. Thereafter, the mixture is filtered through diatomaceous earth and reduced under vacuum to residue. The residue is either taken up in toluene and anhydrous potassium carbonate is added, or is taken up in ethyl acetate or toluene and a tertiary amine base, such as triethylamine, is added. Benzoyl chloride is then added, and after stirring for two hours, the mixture is washed with water and brine, the resulting organic phase is separated, dried, and concentrated under vacuum. The resulting product is dissolved in isopropanol to which Pearlman's catalyst is added, and the mixture is hydrogenated for 24 hours under 40 psi hydrogen to yield paclitaxel.

While the above process removes the various protecting groups on the coupled ester and forms paclitaxel, the present invention provides an improved process which reduces the number of chemical steps in the synthetic process and decreases the total time required therefor. Further, the process of the present invention can be accomplished in a single reaction vessel, thus simplifying the work-up involved in the synthesis.

I. Conversion of Coupled Ester to Paclitaxel

Figure 1:
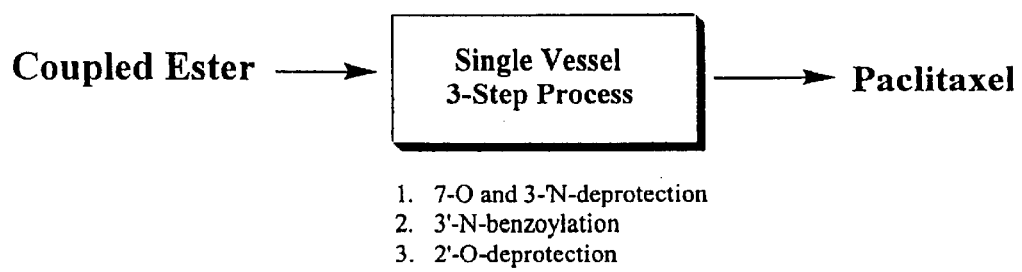
FIG. 1 is a diagram of a single vessel 3-step process according to the present invention.

Specifically, as shown in FIG. 1, the present invention broadly relates to a single vessel 3-step conversion of protected coupled ester to paclitaxel, wherein in a first step the 7-O and 3'-N positions are deprotected, in a second step the 3'-N position is benzoylated, and in a third step the 2'-O position is deprotected.

Figure 2:
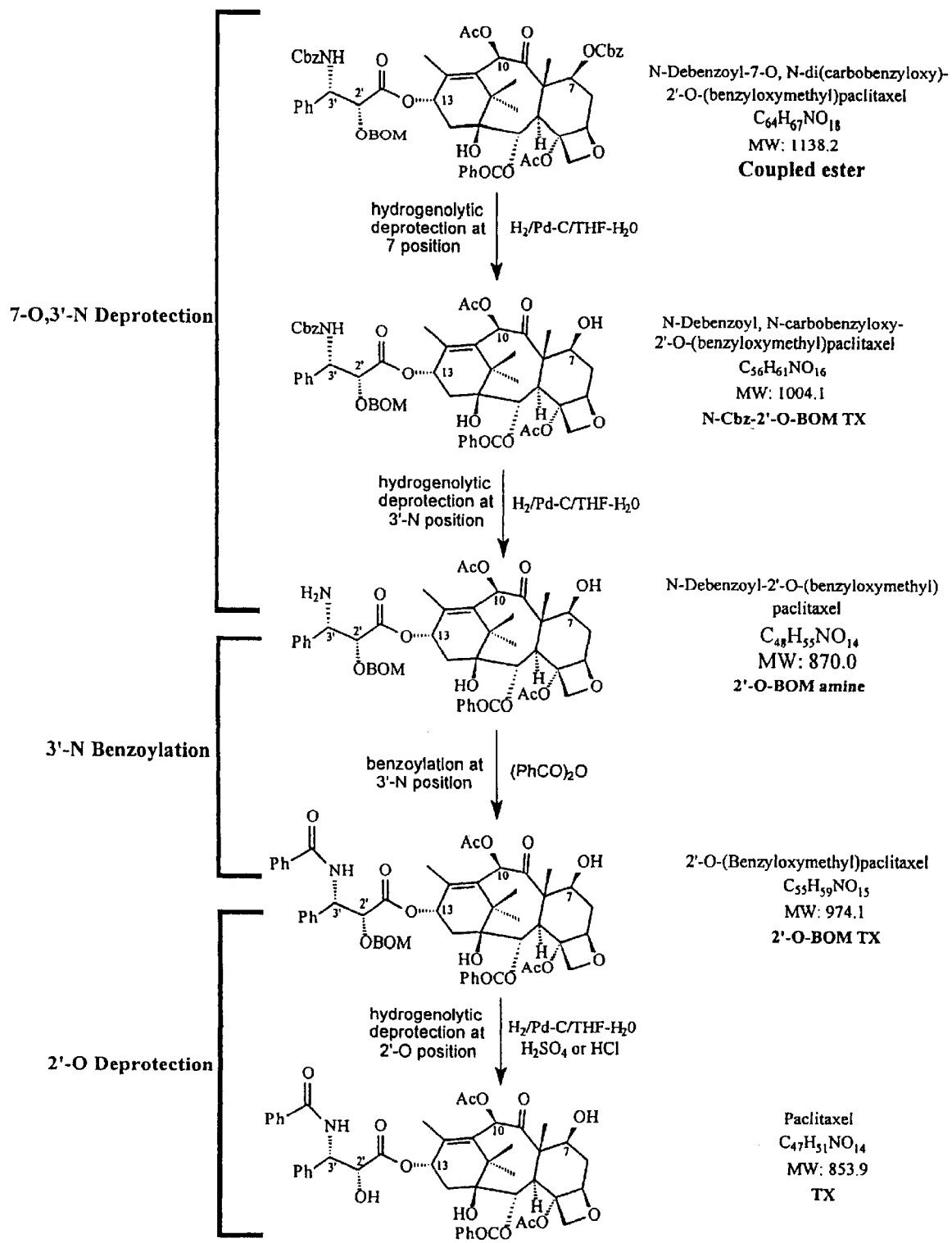
FIG. 2 shows an exemplary preparation of paclitaxel from a protected coupled ester compound according to the present invention.

In the exemplary process, as shown in FIG. 2, the present invention provides a method for converting a protected coupled ester to paclitaxel via hydrogenolytic deprotection of the molecule at 7-O and 3'-N positions (to form a 2'-O-BOM amine), followed by benzoylation of the free 3'-amino group (to form 2'-O-BOM paclitaxel) and hydrogenolytic deprotection at the 2'-O position to form paclitaxel. While FIG. 2 shows a 2'-O-BOM protected coupled ester intermediate, such as formed according to the teachings of U.S. Pat. No. 5,750,737, it should be appreciated that other protected coupled ester intermediates may be converted to paclitaxel according to the process shown in FIG. 2. For example, it should be appreciated that while BOM is shown as the protecting group at the 2' position, the method may be used with other 2'-O-hydrogenatable protecting groups, such as benzyl, substituted benzyl, benzoyl and the like.

1. First Step: 7-O, 3'-N Deprotection

The 7-O, 3'-N-di(CBZ)-2'-O-protected coupled ester intermediate first undergoes hydrogenolytic deprotection at the 7-O and 3'-N positions to remove the CBZ groups as follows:

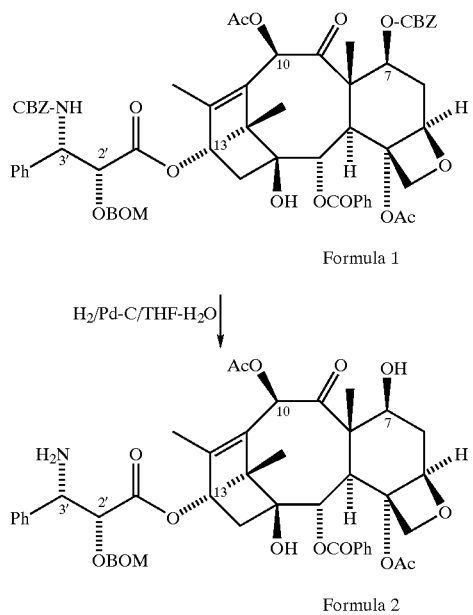

Formula 1

Formula 2

It should be appreciated that a 3'-N-CBZ-2'-O-BOM-7-hydroxy intermediate of the formula:

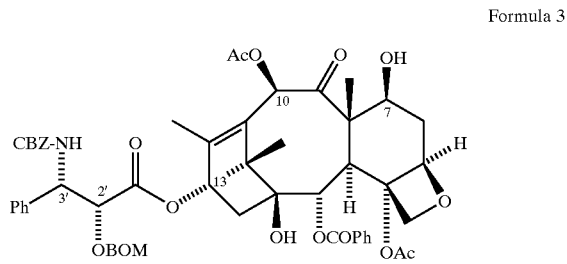

Formula 3 may be formed during this step, as shown in FIG. 2. Additionally, it is believed that a 3'-N-amino-2'-O-BOM-7-O-CBZ paclitaxel intermediate of the formula:

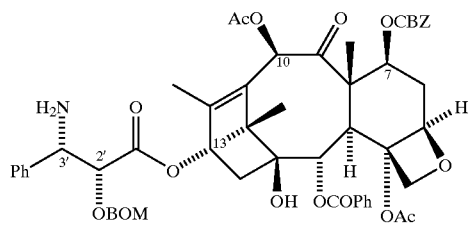

may also be formed during this step.

In the exemplary process, 10.02 g (8.80 mmol) of the protected coupled ester of Formula 1 was dissolved in 180 mL of THF in a reaction vessel, such as a 1 L round bottom flask, equipped with a magnetic stir bar, to which was added 53 mL of water and 16.07 g of 10% Pd/C 50% wet.

While THF is used in the exemplary process herein, it should be appreciated that other solvents may be used. For example, the present invention contemplates the use of solvents having ether functionalities (such as THF), ester functionalities (such as ethyl acetate), or alcohol functionalities (such as methanol, isopropanol and the like). Additionally, while palladium on carbon catalyst is used in the exemplary hydrogenation reactions, the present invention contemplates other hydrogenation catalysts of palladium, as would be understood by the ordinarily skilled artisan. Use of between 30% and 80% mass equivalent of the Pd—C catalyst is contemplated, with 80% preferred. Use of between 10% and 25% water (v/v) is contemplated, with 25% preferred.

The reaction vessel was flushed three times with nitrogen and two times with hydrogen, and the reaction mixture was stirred vigorously under an atmosphere provided by a hydrogen filled balloon for about one hour at room temperature or at a temperature of up to the boiling temperature of the solvent. It is contemplated, however, that the mixture may be stirred for shorter periods of time, as 0% of the protected coupled ester of Formula 1 and only 1.4% of the intermediate of Formula 3 was left remaining in the reaction mixture after 30 minutes, for example, as shown by HPLC data in Table 1, below. At 60 minutes, 0% of compounds of both Formula 1 and Formula 3 was detected.

As shown in FIG. 2, this step results in the 7-O, 3'-N hydrogenolytic deprotection of the protected coupled ester of Formula 1 to form a first intermediate compound having Formula 2. The compound of Formula 2 was detected in 88.9% at 30 minutes and 89.6% at 60 minutes (HPLC area%). A 2'-OH-3'-amine product was also detected in minor amounts as shown in Table 1.

TABLE 1

| Time (min) | Formula 1 | Formula 3 | Formula 2 | 2'OH-3'-amine |
|---|---|---|---|---|
| 0 | 99.5 | — | — | — |
| 30 | 0 | 1.4 | 88.9 | 3.0 |
| 60 | 0 | 0 | 89.6 | 5.6 |

Hydrogen for the hydrogenation reactions herein may be supplied by a variety of methods as would be understood in the art, such as by generation from chemical processes, or supplied by compressed gas cylinders via a hydrogen line at atmospheric pressure or at higher pressures. For example, catalytic hydrogen transfer reduction or transfer hydrogen processes may be used. In particular, the present invention contemplates the use of hydrogen donors, such as ammonium formate, cyclohexene, formic acid, 1,4-cyclohexadiene and cisdecalin, in the presence of Pd/C hydrogenation catalyst.

2. Second Steps 3'-N Benzoylation

The 2'-O-BOM amine of Formula 2 is next benzoylated at the 3'-N position, as follows:

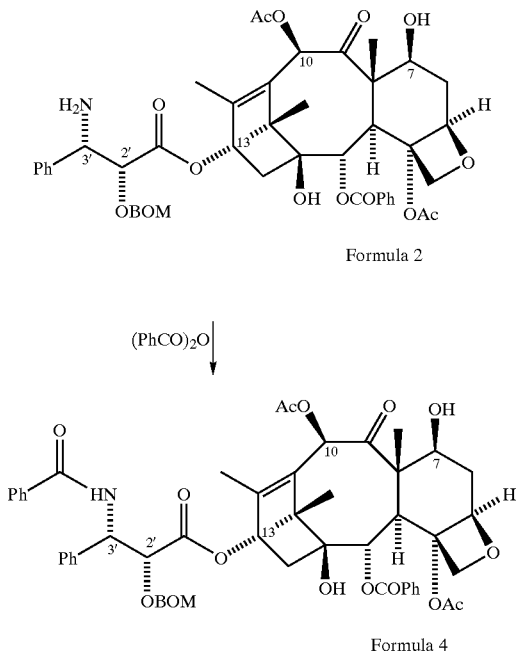

Formula 2

(PhCO)₂O ↓

Formula 4

Here, hydrogen was replaced with nitrogen (by flushing the reaction vessel three times with nitrogen) and a solution of 3.06 g of benzoic anhydride (98% pure, 13.25 mmol) in 10 mL of THF was added to the reaction mixture in the reaction vessel, and stirring was continued for about one hour. The invention contemplates, however, that the mixture can be stirred for as little as 30 minutes, as only small, non-significant progress was observed during the next half-hour, as shown by HPLC data in Table 2, below.

TABLE 2

| Time (min) | Formula 2 | Formula 4 | Paclitaxel |
|---|---|---|---|
| 30 | ~1.6 | 78.3 | 7.6 |
| 60 | ~1.0 | 78.2 | 7.8 |

As discussed below, the invention contemplates the use of between approximately 1.20 mol eq. and 2.40 mol eq. of benzoic anhydride, and specifically 1.50 mol eq. of benzoic anhydride. A direct N-benzoylation of the 2'-O-BOM amine results in a second intermediate compound having Formula 4.

3. Third Step: 2'-O Deprotection

Finally, the 2'-O-BOM paclitaxel of Formula 4 is deprotected at the 2'-O position, as follows:

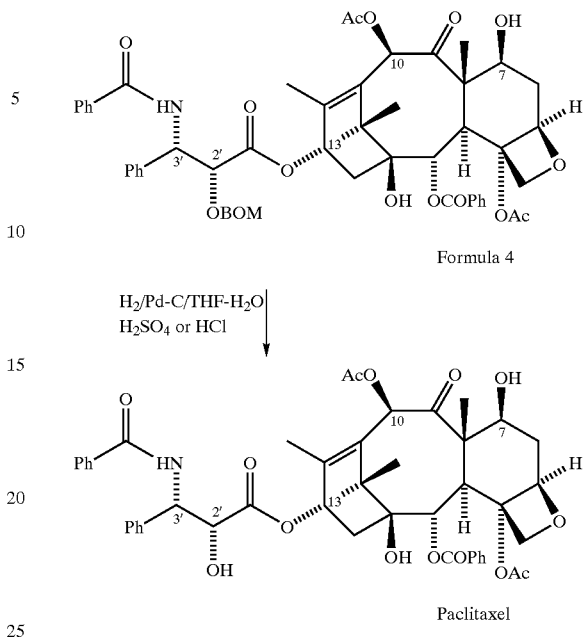

Formula 4

$H_2$/Pd-C/THF-$H_2$O
$H_2SO_4$ or HCl ↓

Paclitaxel

Here, 15.0 mL of 37% hydrochloric acid (181 mmol) was added to the reaction mixture in the reaction vessel, the nitrogen was replaced with hydrogen (by flushing the reaction vessel three times with hydrogen) and the reaction mixture was stirred for about 3 hours under an atmosphere provided by a hydrogen filled balloon. The present invention contemplates, however, that this second hydrogenation may be run for a longer period of time, up to five hours, or a shorter period of time, such as 1 or 2 hours, as only 0.9% and 0.2% of Formula 4 was left after 60 and 120 minutes, respectively, as shown by HPLC data in Table 3, below. Indeed, extension of the reaction time to three hours might result in degradation of some of the paclitaxel product, as shown in Table 3, such that the yield of conversion can be significantly improved by reducing the time of the second hydrogenation from 3 hours down to 1 to 2 hours.

TABLE 3

| Time (min) | Formula 4 | Paclitaxel |
|---|---|---|
| 60 | 0.9 | 91.4 |
| 120 | 0.2 | 91.3 |
| 180 | 0 | 85.3 |

The invention also contemplates the use of between about 5 and 20 mol equivalents of acid, such as hydrochloric or sulfuric acid, with 20 mol eq. of HCl preferred. It should be appreciated, additionally, that the present invention contemplates the use of various other inorganic and organic acids, such as trifluoroacetic acid, p-toluenesulfonic acid, camphorsulfonic acid, and the like.

The balloon was removed, the reaction vessel was then flushed three times with nitrogen and the reaction mixture was filtered through 25 g of Celite. The Celite cake was then washed with 400 mL of ethyl acetate, and the original filtrate and wash were combined into a 1 L separatory funnel. The aqueous phase was removed and the organic phase was washed with water (2×150 mL), then brine (100 mL) and dried over 2 g of anhydrous magnesium sulfate. After filtration and rotaevaporation the product was dried in a vacuum oven for 40h at 40° C to yield 7.99 g of paclitaxel. The true yield of conversion was calculated as 87.4%.

II. Experimental Results

As discussed below, it was found that increasing both the amount of water and palladium catalyst in the hydrogenation mixture significantly reduces time of the conversion of coupled ester to 2'-O-BOM amine and eliminates need for use of acid. More particularly, it was found that introduction of aqueous THF in combination with Pd/C catalyst increases both the yield and the rate of the reaction as compared with the use of anhydrous THF and a Pearlman's catalyst. Additionally, cost of the conversion is decreased by the use of the cheaper palladium on carbon catalyst and by elimination of the use of a costly anhydrous solvent.

Hydrogenolysis carried out in THF containing 25% water by volume in the presence of 80% mass equivalent of 10%/Pd/C catalyst proceeds faster than the reaction performed in the presence of one mol equivalent of trifluoroacetic or p-toluenesulfonic acid, 10% water in THF by volume and 30% mass equivalent of the catalyst. Due to the absence of acid in the post-hydrogenation mixture, a direct N-benzoylation of the resulting 2'-O-BOM amine with benzoic anhydride was performed, instead of using benzoyl chloride and triethylamine for example, and therefore the formation of catalyst poisoning quaternary salts of triethylamine (such as the hydrochloride of triethylamine) was avoided. Consequently, the hydrogenolytic conversion of the resulting 2'-O-BOM paclitaxel to paclitaxel could be accomplished using the same catalyst, reaction medium and reaction vessel, without isolation and purification of the 2'-O-BOM intermediate. Costs attributable to change of the catalyst and reaction medium were thus avoided. The reaction was significantly accelerated by addition of greater amounts of sulfuric acid or, more preferably, hydrochloric acid to the hydrogenation mixture.

All hydrogenation reactions were performed under an atmosphere provided by a hydrogen filled balloon at ambient temperature. All small-scale experiments discussed below were performed using 0.20 g of coupled ester.

1. Effects of Increased Amount of Water and Catalyst on the Conversion of Protected Coupled Ester to 2'-O-ROM Amine Several experiments were performed regarding conversion of coupled ester to paclitaxel in a single reaction vessel without isolation and purification of the 2'-O-BOM-paclitaxel intermediate. During the first hydrogenation step, the presence of acid was eliminated and the effects of introduction of increased amounts of water and catalyst were tested.

Figure 3:
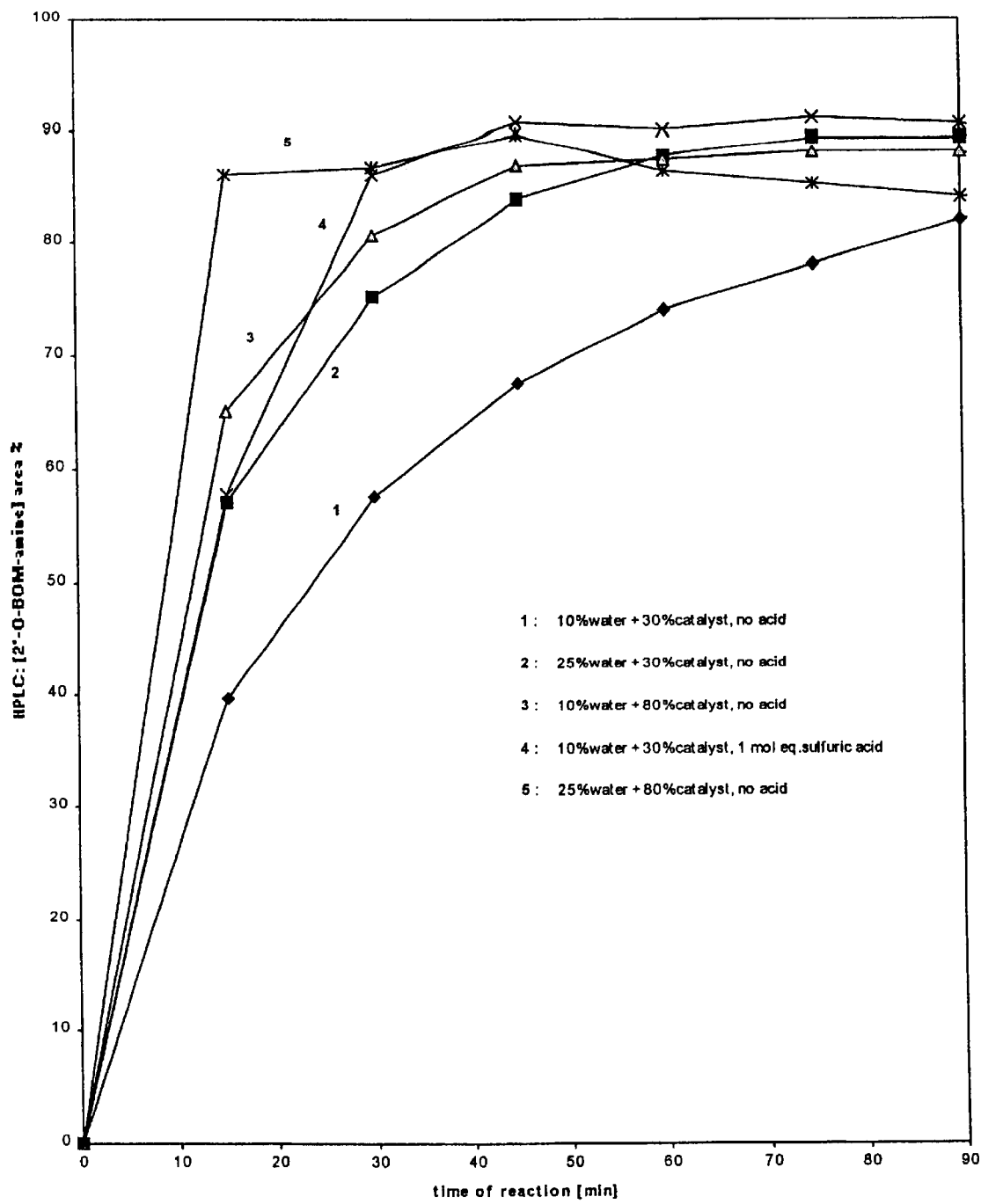
FIG. 3 is a graph showing rates of 2'-O-BOM amine formation under different hydrogenation conditions.

FIG. 3 shows a summary of reactions performed wherein the amounts of water and catalyst were varied, as shown in the legend to FIG. 3, and the presence of acid was investigated with respect to reaction 4.

As seen by comparing reactions 1, 2 and 4 in FIG. 3, by increasing the amount of water from 10% to 25% a similar rate of conversion of the coupled ester is reached without acid as for the rate of the reaction performed in the presence of 10% water and one mol eq. sulfuric acid. As seen by comparing reactions 1, 3 and 4 in FIG. 3, increasing the amount of catalyst to 80% mass eq. in the presence of 10% water with no acid increased the rate of the hydrogenation close to but still below the rate of the reaction performed in the presence of 30% of the catalyst, 10% of water and one mol eq. of sulfuric acid. However, as shown by reaction 5 in FIG. 3, increasing the amount of both water (25% v/v) and the catalyst (80% mass eq.) increased the rate of hydrogenation beyond that of the reaction performed with acid (Reaction 4). To confirm the results of the reactions performed in FIG. 3, fifteen small-scale (0.20 g) and two scale-up (1.0 g and 10.0 g) hydrogenolytic conversions of coupled ester to 2'-O-BOM-amine were performed in the presence of 25% water in THF (v/v) and 80% mass eq. of 10%Pd/C catalyst. Under these conditions, the reaction was complete after about 30 minutes.

2. Use of Benzoic Anhydride for the Conversion of 2'-O-BOM Amine to 2'-O-ROM Paclitaxel The 2'-O-BOM amine of Formula 2 above was N-benzoylated by direct addition of 1.2 mol eq. of benzoic anhydride to the post-hydrogenation reaction mixture in the reaction vessel without removal of the catalyst. Because of the absence of acid in the post-hydrogenation mixture, direct N-benzoylation of the 2'-O-BOM amine with benzoic anhydride was possible. Even in the presence of 25% water (v/v) in the reaction mixture, the benzoylation reaction performed well, as the free primary amino group is much more nucleophilic than water and reacts faster with the anhydride, generating benzoic acid as a by-product. Benzoic acid does not interfere with the next hydrogenation step and is easy to separate from the product stream. The N-benzoylation step is essentially completed in about 30 minutes using benzoic anhydride, although some residual amine and formation of a small amount of an unknown by-product were observed in the reaction mixture. As shown by the HPLC data in Table 4, below, when the time of reaction was increased from 30 to 60 minutes, or the number of mol. equivalents of benzoic anhydride was increased to 2.40 mol eq., partial reduction of the amine residual concentration was observed.

TABLE 4

| Time (min) | mol eq. benz. anh. | 2'-O-BOM paclitaxel | paclitaxel | 2'-O-BOM-amine residual impurities |
|---|---|---|---|---|
| 30 | 2.40 | 80.9 | 5.3 | 0.7;1.6 |
| 30 | 1.50 | 80.3 | 7.5 | 2.6;3.7 |
| 60 | 1.50 | 80.8 | 7.7 | 1.3;3.4 |

3. Effect of Sulfuric Acid and Hydrochloric Acid on the Conversion of 2'-O-BOM Paclitaxel to Paclitaxel In previously described methods of paclitaxel semi-synthesis, the conversion of 2'-O-BOM paclitaxel to paclitaxel was the most complicated step because it required a preliminary purification of the BOM intermediate, elevated pressure of hydrogen, an increased portion of fresh catalyst, new solvent and a long reaction time. These factors suggested against the conversion of a coupled ester to paclitaxel as a single-vessel process.

It was found, however, that addition of increased amounts of mineral acid, such as sulfuric or hydrochloric acid, to the reaction mixture substantially accelerated the rate of the hydrogenolytic removal of the benzyloxymethyl protection from the 2'-O-BOM paclitaxel without significant damage to the starting material or product. Also, because the post-benzoylation reaction mixture did not include tertiary amine or its quaternary salt which act as a catalyst poison, the process of conversion of 2'-O-BOM paclitaxel to paclitaxel could be performed using the same catalyst and reaction medium which were used in the first hydrogenation and N-benzoylation steps. Therefore, the entire conversion of coupled ester to paclitaxel can be run in a single vessel, without isolation or purification of the 2'-O-BOM paclitaxel.

Figure 4:
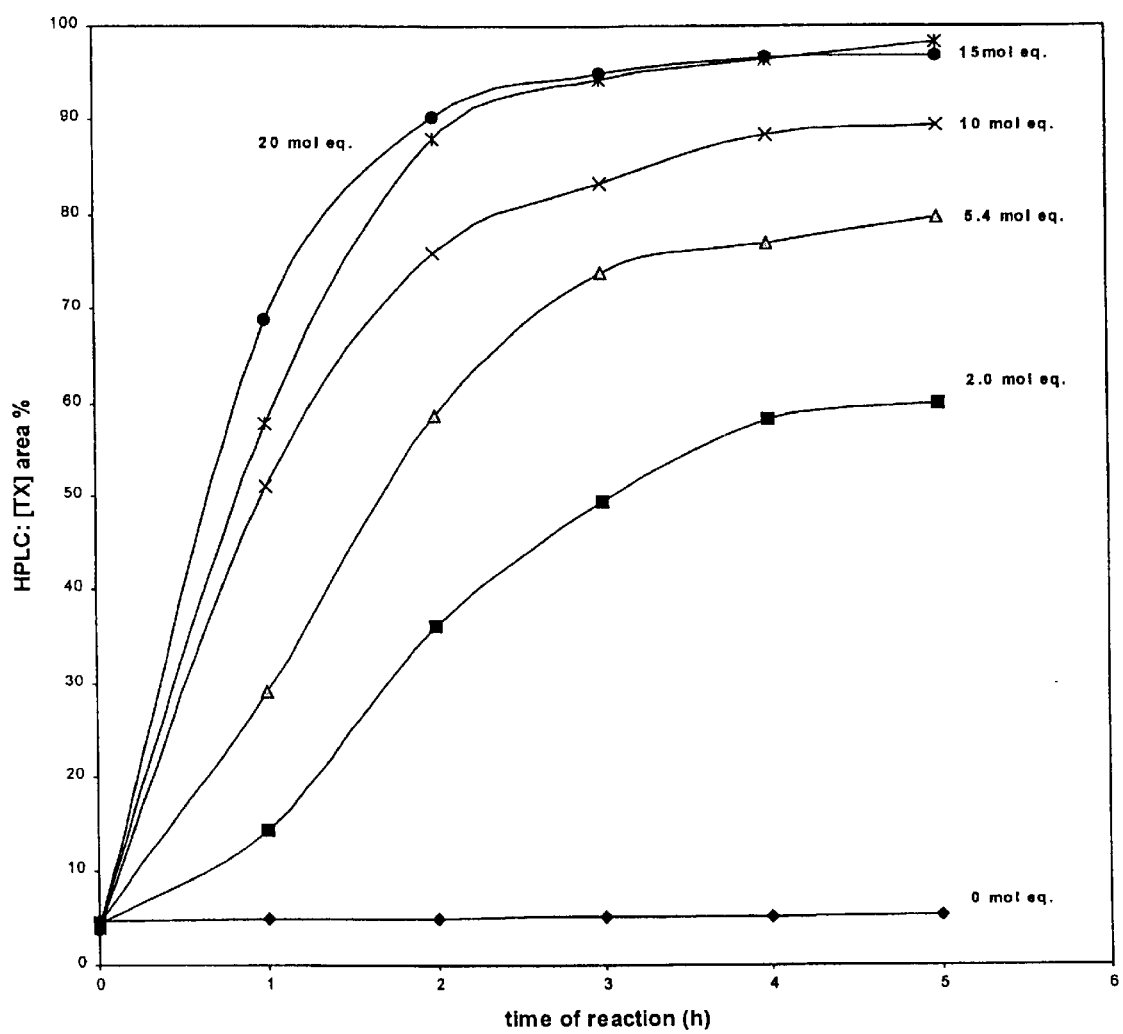
FIG. 4 is a graph showing rates of paclitaxel formation from hydrogenolysis of 2'-O-BOM paclitaxel in the presence of different amounts of sulfuric acid.

As shown in FIG. 4, variable amounts of sulfuric acid were tested in the reaction mixture for this post-benzoylation step. The aqueous acid was added directly to the post-benzoylation mixture and after replacement of nitrogen with hydrogen the hydrogenation was continued under an atmosphere provided by a hydrogen filled balloon at room temperature for 5 hours. The conversion was basically completed after 5 hours although about 2% of 2'-O-BOM paclitaxel still remained unreacted. Increasing the concentration of sulfuric acid in the reaction mixture up to 15 to 20 mol eq. did not lead to complete consumption of the remaining 2% of the substrate. The complete consumption of the 2'-O-BOM derivative could be achieved after prolonged time of hydrogenation, but at the same time the yield of paclitaxel was reduced because of chemical instability of the product under these reaction conditions.

Significant improvement of the hydrogenolytic conversion of 2'-O-BOM paclitaxel to paclitaxel was achieved when the sulfuric acid was replaced with hydrochloric acid. Variable concentrations of hydrochloric acid were tested. The aqueous solution of the acid was added directly to the post-benzoylation mixture and after replacement of nitrogen with hydrogen, the hydrogenation was run under an atmosphere provided by a hydrogen filled balloon at room temperature for 5 hours. In the presence of 10–20 mol eq. of hydrochloric acid, complete consumption of the 2'-O-BOM derivative was achieved after 1 hour. Table 5 shows HPLC data for the formation of 2'-O-BOM paclitaxel and paclitaxel after 60 minutes of reaction in the presence of various concentrations of hydrochloric acid versus sulfuric acid.

TABLE 5

| mol. eq. acid | 2'-O-BOM paclitaxel | | paclitaxel | |
| --- | --- | --- | --- | --- |
| | $H_2SO_4$ | HCl | $H_2SO_4$ | HCl |
| 5 | 63.7 | 5.8 | 29.2 | 94.2 |
| 10 | 41.2 | 0 | 51.1 | ~100 |
| 15 | 40.7 | 0 | 57.9 | 98.8 |
| 20 | 31.2 | 0 | 68.8 | ~100 |

Accordingly, based on the experimental results, conversion of protected coupled ester to paclitaxel in a single vessel without isolation and purification of the 2'-O-BOM paclitaxel intermediate can also be performed, for example, as follows:

A solution of 0.20 g of the protected coupled ester in 25% (v/v) aqueous THF and 80% mass equivalent of 10% Pd/C is hydrogenated for 30 minutes at room temperature under an atmosphere provided by a hydrogen filled balloon. After replacement of hydrogen with nitrogen, a solution of 1.2 mol eq. of benzoic anhydride in THF is added and after 30 minutes of stirring, an aqueous solution of sulfuric acid or hydrochloric acid is added and the mixture is hydrogenated at room temperature for five hours under an atmosphere provided by a hydrogen filled balloon.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained therein.

We claim:

1. A method of producing paclitaxel from a protected coupled ester compound having a formula:

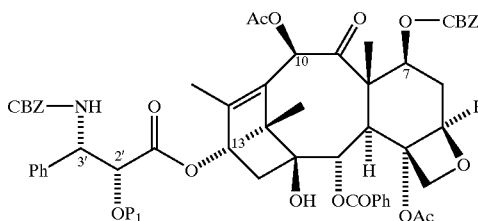

wherein $P_1$ is a hydrogenatable protecting group, comprising the steps of:

(a) deprotecting the 7-O-position and 3'-N-position of the protected coupled ester compound to form a first intermediate compound having a formula:

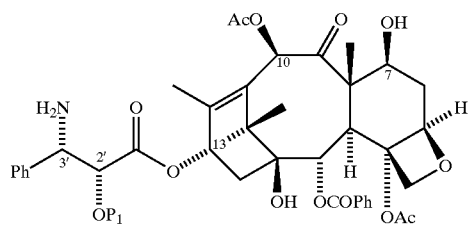

wherein $P_1$ is said hydrogenatable protecting group;

(b) benzoylating said first intermediate compound at the 3'-N-position thereby to form a second intermediate compound having the formula:

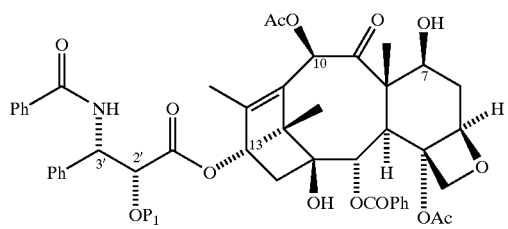

wherein $P_1$ is said hydrogenatable protecting group; and (c) deprotecting said second intermediate compound by replacing $P_1$ with hydrogen in the presence of an acid, thereby to produce paclitaxel.

2. A method according to claim 1 wherein $P_1$ is selected from the group consisting of benzyl, substituted benzyl, benzyloxymethyl, and benzoyl.

3. A method according to claim 1 wherein the protected coupled ester compound is dissolved in a solvent to form a first solution prior to the step of deprotecting the 7-O-position and 3'-N-position of the protected coupled ester compound.

4. A method according to claim 3 wherein said solvent includes a functional group selected from the group consisting of an ether, an ester and an alcohol.

5. A method according to claim 4 wherein said solvent is selected from the group consisting of THF, ethyl acetate, methanol and isopropanol.

6. A method according to claim 3 wherein said solvent is an anhydrous solvent and wherein said solvent is made hydrous by adding water thereto in an amount such that said water and said solvent are not immiscible.

7. A method according to claim 3 wherein water and a hydrogenation catalyst are added to said first solution to form a first reaction mixture prior to the step of deprotecting the 7-O-position and 3'-N-position of the protected coupled ester compound.

8. A method according to claim 7 wherein said catalyst is selected from the group consisting of Pearlman's catalyst and palladium on carbon catalyst.

9. A process according to claim 7 wherein said catalyst is 10% Pd/C 50% wet.

10. A method according to claim 7 wherein said catalyst is added in an amount of 30% to 80% mass equivalent of said protected coupled ester.

11. A method according to claim 7 wherein said water is added in an amount of 10% to 25% by volume of said solvent.

12. A method according to claim 1 wherein the step of deprotecting the 7-O-position and 3'-N-position of the protected coupled ester compound is accomplished by hydrogenolytic deprotection.

13. A method according to claim 1 wherein the protected coupled ester compound is dissolved in THF to form a first solution to which water and a hydrogenation catalyst are added to form a first reaction mixture prior to the step of deprotecting the 7-O-position and 3'-N-position of the protected coupled ester compound, and wherein the step of deprotecting the 7-O-position and 3'-N-position of the protected coupled ester compound is accomplished by stirring said first reaction mixture under a hydrogen atmosphere for 30 to 60 minutes.

14. A method according to claim 1 wherein the step of benzoylating said first intermediate compound is accomplished by mixing benzoic anhydride with said first intermediate compound to form a second reaction mixture.

15. A method according to claim 14 wherein 1.20 to 2.40 mol equivalents of benzoic anhydride is mixed with said first intermediate compound.

16. A method according to claim 14 wherein said second reaction mixture is stirred for 30 to 60 minutes under an inert atmosphere.

17. A method according to claim 1 wherein the step of deprotecting said second intermediate compound is accomplished by mixing said second intermediate compound with a selected quantity of said acid thereby to form a third reaction mixture and thereafter stirring said third reaction mixture under a hydrogen atmosphere.

18. A method according to claim 17 wherein said third reaction mixture is stirred for one to five hours.

19. A method according to claim 18 wherein said third reaction mixture is stirred for one to two hours.

20. A method according to claim 17 wherein said second intermediate compound is mixed with 5 to 20 mol equivalents of said acid.

21. A method according to claim 17 wherein said acid is selected from a group consisting of an inorganic acid and an organic acid.

22. A method according to claim 17 wherein said acid is selected from a group consisting of sulfuric acid and hydrochloric acid.

23. A method of producing paclitaxel, comprising the steps of:
(a) stirring a first reaction mixture of a solvent, water, a hydrogenation catalyst and a protected coupled ester compound having a formula:

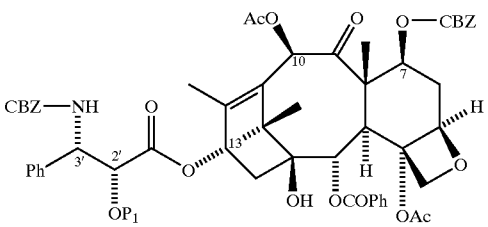

wherein $P_1$ is a hydrogenatable protecting group, in a reaction vessel under a hydrogen atmosphere;

(b) adding a benzoylating agent to said reaction vessel to form a second reaction mixture and stirring said second reaction mixture; and (c) adding acid to said reaction vessel to form a third reaction mixture and stirring said third reaction mixture in said reaction vessel under a hydrogen atmosphere thereby to produce paclitaxel.

24. A method according to claim 23 wherein said water is present in said first reaction mixture in 10% to 25% by volume of said solvent.

25. A method according to claim 23 wherein said catalyst is present in said first reaction mixture in 30% to 80% mass equivalent of said protected coupled ester.

26. A method according to claim 23 wherein said water is present in said first reaction mixture in 25% by volume of said solvent, wherein said catalyst is present in said first reaction mixture in 80% mass equivalent of said protected coupled ester, and wherein said first reaction mixture is stirred under an atmosphere of hydrogen at room temperature for 30 to 60 minutes.

27. A method according to claim 23 wherein said benzoylating agent is benzoic anhydride.

28. A method according to claim 27 wherein the step of adding said benzoylating agent includes adding a solution of 1.2 to 2.4 mol equivalent of benzoic anhydride in THF to said reaction vessel.

29. A method according to claim 23 wherein said second reaction mixture is stirred for 30 to 60 minutes under an inert atmosphere.

30. A method according to claim 23 wherein 5 to 20 mol equivalents of acid is added to said reaction vessel to form said third reaction mixture.

31. A method according to claim 30 wherein said third reaction mixture is stirred for one to five hours under said hydrogen atmosphere.

32. A method according to claim 23 wherein a compound having the formula:

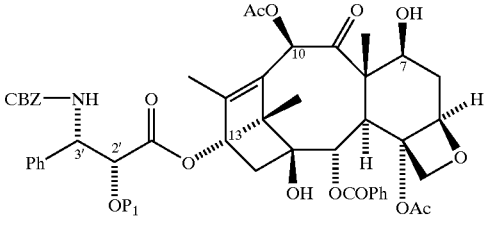

wherein $P_1$ is a hydrogenatable protecting group, is formed in said reaction vessel during the step of stirring said first reaction mixture under said hydrogen atmosphere.

33. A method according to claim 23 wherein a compound having the formula:

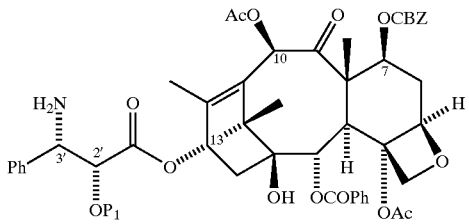

wherein $P_1$ is a hydrogenatable protecting group, is formed in said reaction vessel during the step of stirring said first reaction mixture under said hydrogen atmosphere.

34. A process of producing paclitaxel from a protected coupled ester compound having the formula:

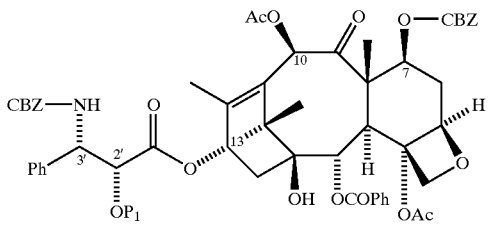

wherein $P_1$ is a hydrogenatable protecting group, consisting of the steps of:
  (a) replacing the 7-O-CBZ and 3'-N-CBZ groups with hydrogen to form a first intermediate compound having a formula:

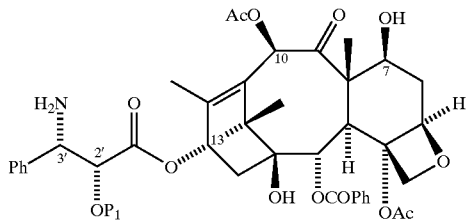

wherein $P_1$ is said hydrogenatable protecting group;
  (b) benzoylating said first intermediate compound at the 3'-N-position thereby to form a second intermediate compound having the formula:

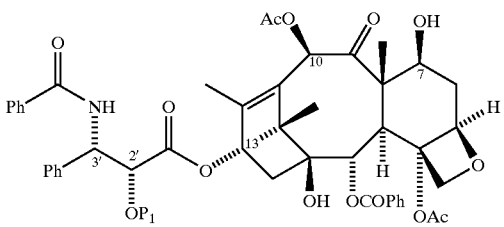

wherein $P_1$ is said hydrogenatable protecting group; and
  (c) replacing $P_1$ with hydrogen, thereby to produce paclitaxel.

* * * * *